United States Patent [19]

Nakano et al.

[11] Patent Number: 4,787,977

[45] Date of Patent: Nov. 29, 1988

[54] BLOOD-PURIFYING MEMBRANE

[75] Inventors: Hiroo Nakano, Nobeoka; Kazushige Seita, Tokyo; Kazuo Imamura; Tetsuo Watanabe, both of Nobeoka, all of Japan

[73] Assignee: Asahi Kasei Kogyo Kabushiki Kaisha, Osaka, Japan

[21] Appl. No.: 797,973

[22] Filed: Nov. 14, 1985

[51] Int. Cl.$^4$ .................. A61M 1/34; B01D 13/01
[52] U.S. Cl. .................. 210/500.23; 210/500.29; 210/500.37
[58] Field of Search .............. 210/500.29, 500.34, 210/500.37, 500.38, 500.39, 500.42, 500.43, 500.24, 500.23; 427/244–246; 521/84.1

[56] References Cited

U.S. PATENT DOCUMENTS 4,326,958 4/1982 Kawahara et al. ............ 210/500.29
4,459,210 7/1984 Murakami et al. ............ 210/500.42

FOREIGN PATENT DOCUMENTS 3341113 5/1985 Fed. Rep. of Germany ..................... 210/500.24

*Primary Examiner*—Ivars Cintins
*Attorney, Agent, or Firm*—Finnegan, Henderson, Farabow, Garrett & Dunner

[57] ABSTRACT

A blood-purifying regenerated cellulose membrane, in which the occurrence of the leukopenia phenomenon and the activation of the complement system are moderated, is prepared by applying a solution of a polymeric substance comprising as one component units derived from one or more basic vinyl monomers having an amino group in the side chain in an organic solvent to a regenerated cellulose membrane, removing the excessive solution, and then fixing the polymeric substance to the regenerated cellulose membrane.

13 Claims, No Drawings

BLOOD-PURIFYING MEMBRANE

BACKGROUND OF THE INVENTION

1. Field of the Invention

The present invention relates to an improved blood-purifying regenerated cellulose membrane and a process for the preparation thereof. More particularly, it relates to a blood-purifying regenerated cellulose which is improved in the compatibility with blood and a process for the preparation thereof.

2. Description of the Related Art

Recently, hemodialysis therapy for patients with end-stage renal disease has made rapid progress while being supported by advances of dialyzers, dialyzing instruments, and dialyzing technique, and has made great contributions to the survival and rehabilitation of patients with end-stage renal disease. Regenerated cellulose membranes, especially cuprammonium regenerated cellulose membrane, have played an important role in the development of the hemodialysis therapy, and the hemodialysis therapy has been and is being performed mainly by using cuprammonium regenerated cellulose membranes. This is because this membrane has an excellent dialysis performance and a high safety, supported by past actual results over a long term.

However, various problems are left unsolved in spite of the development of the hemodialysis therapy. For example, there can be mentioned various side effects considered to be caused by an anticoagulant which is administered in large quantities for a long time, the phenomenon of complement activation and leukopenia (i.e., white cell drop), both of which occur transiently during the initial phase of the dialysis procedure, although the clinical relevance of these phenomena has not been elucidated, that is, the phenomenon of leukopenia in which the number of leukocytes is reduced at the initial phase of the hemodialysis: this reduction is most prominent 15 to 20 minutes after the onset of the hemodialysis and the number is returned to the predialysis level within about 1 hour.

These problems are not serious in the case of membranes of synthetic polymers such as polymethyl methacrylate, polyacrylonitrile, and poly(ethylene-vinyl alcohol), but these synthetic polymer membranes are defective in that the mechanical strength is poor, pinholes are readily formed, the sterilization method is limited because of insufficient heat resistance, and the application method is limited by an improper balance among the properties, especially an improper balance between the water permeability and the substance permeability.

Modifications of surfaces of regenerated cellulose membranes have been proposed. For example, a method in which the membrane surface is modified with heparin to impart an antithrombotic property to the membrane surface is proposed in U.S. Pat. No. 3,616,935 and Japanese unexamined patent publication No. 51-194. According to this method, however, satisfactory results cannot be obtained and the manufacturing cost is high, and therefore, membranes of this type have not been practically used. Recently, as means for moderating the phenomenon of the leukopenia, there have been recently proposed a regenerated cellulose membrane coated with an oil-soluble vitamin (see Japanese unexamined patent publication No. 60-80462) and a regenerated cellulose membrane to which a polymer acid is chemically bonded (see Japanese unexamined patent publication No. 60-118203). The former proposal is insufficient in the stability of the coated membrane, and the latter proposal has problems such that the process steps are complicated and the manufacturing cost is high.

SUMMARY OF THE INVENTION

Therefore, it is a primary object of the present invention to provide a blood-purifying regenerated cellulose membrane in which the occurrence of the leukopenia phenomenon and the activation of the complement system are moderated, and a process for preparing this membrane by modifying the surface of the regenerated cellulose membrane without significant loss of its excellent dialysis performance.

In one aspect of the present invention, there is provided a blood-purifying regenerated cellulose membrane, which comprises a membrane composed of regenerated cellulose, blood contacting surface of the membrane being coated with a polymeric substance comprising as one component units derived from one or more basic vinyl monomers having an amino group in the side chain.

In another aspect of the present invention, there is provided a process of the preparation of blood-purifying regenerated cellulose membranes, which comprises applying a solution of a polymeric substance comprising as one component units derived from one or more basic vinyl monomers having an amino group in the side chain in an organic solvent to a regenerated cellulose membrane, removing the excessive solution, and then fixing the polymeric substance to the regenerated cellulose membrane.

DESCRIPTION OF THE PREFERRED EMBODIMENTS

The "regenerated cellulose" used in the present invention is a product obtained by chemically or physically modifying natural cellulose and then regenerating the modified cellulose into cellulose. For example, there are included cuprammonium regenerated cellulose, viscose rayon, and saponified cellulose ester. However, cuprammonium regenerated cellulose is preferred because of its high dialysis performance and high safety, supported by past actual results over a long time.

With reference to the shape of the regenerated cellulose membrane, any types of membrane such as a flat sheet or a hollow fiber can be used. However, in view of the flexibility of the membrane as the blood-purifying membrane, a hollow fiber membrane is preferable.

As the basic vinyl monomer having an amino group in the side chain, any of vinyl monomers having a primary amino group, a secondary amino group, or a tertiary amino group can be used. For example, there can be mentioned acrylic acid derivatives, methacrylic acid derivatives, acrylic acid amide derivatives and methacrylic acid amide derivatives, which have an amino group in the side chain, vinyl compounds having a nitrogen-containing aromatic ring group such as a pyridyl or imidazolinyl group in the side chain, and styrene derivatives substituted with an amino group. Furthermore, a monomer in which an amino group can be introduced by amination after polymerization, for example, chloromethylstyrene, may be used. Vinyl monomers having a tertiary amino group are most preferred, and there are preferably used dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, diethylaminopropyl methacrylate, 3-dimethylamino-2-hydroxypropyl acrylate, 3-dimethylamino-2-hydroxypropyl methacrylate, 3-diethylamino-2-hydroxypropyl acrylate, 3-diethylamino-2-hydroxypropyl methacrylate, N-dimethylaminoethyl acrylic acid amide, N-dimethylaminoethyl methacrylic acid amide, N-diethylaminoethyl acrylic acid amide, N-diethylaminoethyl methacrylic acid amide, and styrene derivatives represented by the following formula:

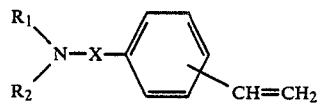

wherein $R_1$ represents $CH_3$ or $CH_3CH_2$, and X represents $-(CH_2)_l-$ in which l is an interger of from 1 to 3.

The above-mentioned basic vinyl monomer or monomers are the indispensable component of the polymeric substance used in the present invention, and it is preferred that the vinyl monomer or monomers are contained in an amount of at least 0.1% by weight, more preferably at least 1% by weight.

The polymeric substance used in the present invention includes a homopolymer of the above-mentioned amino group-containing vinyl monomer, a copolymer consisting of at least two of the above-mentioned amino group-containing vinyl monomers and a copolymer of the above-mentioned amino group-containing vinyl monomer or monomers with one or more copolymerizable other vinyl monomers. The polymeric substance may be used either singly or in combination.

A vinyl monomer having a polyalkylene glycol chain in the side chain is preferred as the above-mentioned comonomer. As the polyalkylene glycol chain, there can be mentioned polyethylene glycol, polypropylene glycol, and polybutylene glycol, and the terminal groups be any of the hydroxyl, methoxy, and ethoxy groups. Accordingly, as the vinyl monomer, there can be used acrylic acid or methacrylic acid derivatives represented by the following formula:

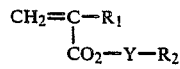

wherein $R_1$ represents H or $CH_3$, $R_2$ represents H or $CH_3$, and Y represents $-(CH_2CH_2O)_m-$ or

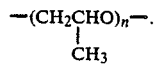

It is preferred that the chain length (i.e., n or m in the above formula) be 2 to 1000, more preferably 2 to 200.

It is preferred that the content of the above-mentioned vinyl monomer in the polymeric substance is 0.5 to 50% by weight, more preferably 1 to 50% by weight.

Other vinyl monomers may be used as the comonomer to be copolymerized with the basic vinyl monomer having an amino group in the side chain. For example, there are preferably used acrylic acid derivatives, methacrylic acid derivatives, acrylic acid amide and its derivatives, methacrylic acid amide and its derivatives, styrene, vinyl acetate, and N-vinylpyrrolidone. Alkyl acrylates and methacrylates having 1 to 12 carbon atoms in the alkyl group, N-alkyl acrylic and methacrylic acid amides having 1 to 12 carbon atoms in the alkyl group, 2-hydroxyethyl methacrylate, and n-vinylpyrrolidone are especially preferred.

These comonomers may be used singly, or two or more of them may be used in combination. It is especially preferred that a vinyl monomer having a polyalkylene glycol chain in the side chain and a vinyl monomer as described above be used in combination.

The polymeric substance used in the present invention may be synthesized according to the known radical polymerization or ion polymerization process or the like.

The amount of the polymeric substance coated on the regenerated cellulose membrane is 50 to 5000 ppm, preferably 70 to 1000 ppm, based on the regenerated cellulose membrane. If the amount of the polymeric substance is smaller than 50 ppm, the effect of improving the compatibility with blood is not sufficient. If the amount of the polymeric substance is larger than 5000 ppm, the dialysis performance is reduced.

In order to form the above-mentioned coating in the present invention, it is preferred that the polymeric substance be dissolved in a solvent described hereinafter at a concentration of 0.01 to 5 weight/volume% (hereinafter referred to as "W/v%").

In the present invention, at least one of the above-mentioned polymeric substance is coated on the regenerated cellulose membrane by dissolving the polymeric substance uniformly in an organic solvent and applying the formed polymer solution to the regenerated cellulose membrane. The application can be accomplished according to a method in which the polymeric substance in the state of a polymer solution is contacted with a membrane to cause adhesion or absorption of the polymeric substance. This method includes, for example, a method in which a membrane is immersed in the polymer solution, a method in which the polymer solution is coated on a membrane, and a method in which the polymer solution is passed through a hollow fiber.

As the solvent to be used for the coating operation (hereinafter referred to as "coating solvent"), any of solvents capable of dissolving the polymeric substance therein can be used. An appropriate solvent is selected while taking the ease of fixation of the polymer described below, the ease of removal, and the safety of the small amount of the residual solvent into consideration. In the present invention, as the coating solvent, there are preferably used lower alcohols such as methanol and ethanol, acetone, ethyl acetate and chlorofluorohydrocarbon solvents such as trichlorofluoromethane, 1,1,2-trichloro-1,2,2-trifluoroethane, and 1,1,2,2-tetrachloro-1,2-difluoroethane. A solvent formed by incorporating 0 to 100% of ethanol into at least one chlorofluorohydrocarbon solvent selected from trichlorofluoromethane, 1,1,2-trichloro-1,2,2-trifluoroethane, and 1,1,2,2-tetrachloro-1,2-difluoroethane is more preferable.

After the polymer solution has been applied to the regenerated cellulose membrane, the excessive polymer solution is removed from the membrane surface. If this operation is not appropriately performed, the thickness of the coating layer becomes uneven to cause variance of the performance, and there is a risk of falling off of the coating layer while the membrane is used. This removal operation is accomplished by a method utilizing a centrifugal force of a centrifugal separator or the like, a method utilizing compressed air or air suction, or a method in which the solution is absorbed in an absorbent paper or the like.

Fixation of the polymer to the surface of the regenerated cellulose membrane is accomplished by removal of the coating solvent. If the coating solvent is a volatile solvent, vacuum drying, air drying or heat-drying may be adopted. If the coating solvent has a relatively high boiling point, there may be adopted a method in which the membrane is washed with the coating solvent free of the polymer, if necessary; washed with a volatile organic solvent having a good miscibility with the coating solvent; and then dried in the same manner as described above.

In order to increase the uniformity of the coating layer, it is preferred that the operations of application of the polymer solution, removal of the excessive polymer solution, and fixation of the polymer be repeated at least 2 times. If these operations including the heat treatment described below are repeated at least 2 times, the uniformity of the coating layer is enhanced.

For fixation of the polymer, it is preferred that the heat treatment be conducted after the coating solvent has been removed. The heat treatment is effective for ensuring fixation of the polymer, preventing falling of the coating layer and enhancing the compatibility with blood. It is preferred that the heat treatment be carried out at 50° to 150° C., more preferably 70° to 130° C. Either dry heating or steam heating may be adopted, and a high frequency heating method and a far infrared heating method are effective. The heat treatment time is determined according to the intended treatment effect. The heat treatment time is ordinarily scores of seconds to several hours and preferably 1 to 60 minutes. If the steam sterilization is performed, a sufficient heat treatment effect is often attained even though the heat treatment is omitted.

The above-mentioned preparation process may be similarly applied, whether the blood-contacting surface to be coated may be the inner surface or the outer surface of a hollow fiber. Moreover, the preparation processing similarly adopted in the case where hollow fibers are set in a dialyzer.

The present invention will now be described in detail with reference to the following examples.

Note, the properties referred to in the examples were determined according to the following methods.

(1) Water permeability

Both ends of a bundle of 100 hollow fibers were set by an adhesive to form a module, water was filled in the interiors of the fibers, and one end of the bundle was closed. Water was charged from the open end under a pressure of 200 mmHg and the amount of water permeating per unit of time was measured. The membrane area of the fibers was calculated from the measured values of the inner diameter and the effective length of the fibers.

(2) Clearance

A module was prepared in the same manner as described in (1) above, and the test was carried out by using an aqueous solution containing 100 ppm of urea or 100 ppm of vitamin $B_{12}$ ($VB_{12}$). The concentration in the dialyzate was determined from the absorbance measured by a spectrophotometer, and the clearance was calculated according to the following formula:

$$\text{Clearance} = \frac{\text{(concentration in dialyzate)} \times \text{(amount of dialyzate per minute)}}{\text{(concentration before dialysis)}}$$

(3) Complement consumption ratio

The regenerated cellulose membrane was placed in serum so that the surface area was 80 cm² per ml of serum, and the mixture was shaken at 37° C. for 1 hour. The 50% hemolytic complement value (CH50) was determined as the value of the complement in serum by the method of Meyer et al. (Experimental Immunochemistry, page 133, Thomas, 1961), and the decrease from the value of the control was expressed as the complement consumption ratio.

Note, in the following examples, the composition of each copolymer is expressed by the weight ratio, and 1,1,2-trichloro-1,2,2-trifluoroethane is expressed as "Freon R-113" according to popular nomenclature.

EXAMPLE 1

A bundle (10,000 hollow fibers, 30 cm in length) of dry cuprammonium regenerated cellulose hollow fibers (200 μm in inner diameter, 13 μm in membrane thickness) was immersed in a 0.05 w/v% ethanol solution of poly(dimethylaminoethyl methacrylate) at room temperature for about 10 minutes, the excessive solution was removed by a centrifugal separator, and the bundle was dried at 40° C. under 750 mmHg in a vacuum dryer for 1 hour. The bundle was then heat-treated at 120° C. for 10 minutes in a dry-heating dryer.

With respect to the thus-coated hollow fiber membrane and the untreated hollow fiber membrane, the dialysis performance and complement consumption ratio were determined. The obtained results are shown in Table 1.

TABLE 1

| | Example 1 | Untreated hollow fiber membrane |
|---|---|---|
| Water permeability (ml/m² · mmHg · hr) | 3.8 | 4.0 |
| Urea clearance (ml/min) | 160 | 164 |
| $VB_{12}$ clearance (ml/min) | 39 | 44 |
| Complement consumption ratio | 14 | 40 |
| Coating amount (ppm) | 210 | 0 |

EXAMPLES 2, 3 and 4

The coating treatment was carried out in the same manner as described in Example 1 except that a 0.05 w/v% ethanol solution of poly(diethylaminoethyl methacrylate) (Example 2), a 0.05 w/v% ethanol solution of poly(3-dimethylamino-2-hydroxypropyl methacrylate) (Example 3) or a 0.05 w/v% ethanol solution of poly(dimethylaminoethyl-diethylaminoethyl methacrylate) (45.9/54.1 weight ratio) (Example 4) was used as the polymer solution. The dialysis performance and complement consumption ratio of the obtained hollow fiber membrane were measured. The obtained results are shown in Table 2.

TABLE 2

| | Example 2 | Example 3 | Example 4 |
|---|---|---|---|
| Water permeability (ml/m² · mmHg · hr) | 3.9 | 3.8 | 3.8 |
| Urea clearance (ml/min) | 160 | 162 | 160 |

TABLE 2-continued

|  | Example 2 | Example 3 | Example 4 |
|---|---|---|---|
| $VB_{12}$ clearance (ml/min) | 40 | 39 | 39 |
| Complement consumption ratio | 15 | 16 | 14 |
| Coating amount (ppm) | 205 | 200 | 220 |

EXAMPLES 5, 6 and 7

The coating treatment was carried out in the same manner as described in Example 1 except that poly(diethylaminoethyl methacrylate-methoxypolyethylene glycol (polymerization degree=23) methacrylate) (95/5 weight ratio) (Example 5), poly(dimethylaminoethyl methacrylate-methoxypolyethylene glycol (polymerization degree=23) methacrylate) (95/5 weight ratio) (Example 6) or poly(dimethylaminoethyl methacrylate-methoxypolyethylene glycol (polymerization degree=90) methacrylate) (95/5 weight ratio) (Example 7) was used as the polymer. The dialysis performance and complement consumption ratio of the hollow fiber membrane were measured. The obtained results are shown in Table 3.

TABLE 3

|  | Example 5 | Example 6 | Example 7 |
|---|---|---|---|
| Water permeability ($ml/m^2 \cdot mmHg \cdot hr$) | 4.0 | 4.0 | 3.9 |
| Urea clearance (ml/min) | 161 | 161 | 158 |
| $VB_{12}$ clearance | 41 | 40 | 39 |
| Complement consumption ratio | 12 | 12 | 15 |
| Coating amount (ppm) | 210 | 210 | 215 |

EXAMPLES 8, 9 and 10

The coating treatment was carried out in the same manner as described in Example 1 except that a 0.05 w/v% solution of poly(methyl methacrylate-dimethylaminoethyl methacrylate) (85.1/14.9) weight ratio) in a Freon R-113-ethanol (80/20 weight ratio) solution (Example 8), a 0.05 w/v% solution of poly(ethyl methacrylate-dimethylaminoethyl methacrylate) (86.7/13.3 weight ratio) in a Freon R-113-ethanol (96/4 weight ratio) solution (Example 9) or a 0.05 w/v% solution of poly(butyl methacrylate-diethylaminoethyl methacrylate) (88.2/11.8 weight ratio) in a Freon R-113-ethanol (96/4 weight ratio) solution (Example 10) was used as the polymer solution. The dialysis performance and complement consumption ratio of the obtained hollow yarn membrane were measured. The obtained results are shown in Table 4.

TABLE 4

|  | Example 8 | Example 9 | Example 10 |
|---|---|---|---|
| Water permeability ($ml/m^2 \cdot mmHg \cdot hr$) | 3.8 | 3.8 | 3.7 |
| Urea clearance (ml/min) | 161 | 160 | 158 |
| $VB_{12}$ clearance (ml/min) | 38 | 37 | 36 |
| Complement consumption ratio | 14 | 12 | 13 |
| Coating amount (ppm) | 170 | 160 | 155 |

EXAMPLES 11, 12 and 13

The coating treatment was carried out in the same manner as described in Example 1 except that a 0.05 w/v% ethanol solution of poly(2-hydroxyethyl methacrylate-diethylaminoethyl methacrylate) (86.3/13.7 weight ratio) (Example 11), a 0.05 w/v% ethanol solution of poly(N-vinylpyrrolidone-dimethylaminoethyl methacrylate) (86.4/13.6 weight ratio) (Example 12) or a 0.05 w/v% solution of poly(methyl methacrylate-diethylaminoethyl methacrylate) (82.9/17.1 weight ratio) in a Freon R-113-ethanol (80/20 weight ratio) solution (Example 13) was used as the polymer solution. The dialysis performance and complement consumption ratio of the obtained hollow fiber membrane were measured. The obtained results are shown in Table 5.

TABLE 5

|  | Example 11 | Example 12 | Example 13 |
|---|---|---|---|
| Water permeability ($ml/m^2 \cdot mmHg \cdot hr$) | 3.9 | 3.9 | 3.8 |
| Urea clearance (ml/min) | 160 | 161 | 159 |
| $VB_{12}$ clearance (ml/min) | 39 | 40 | 38 |
| Complement consumption ratio | 15 | 14 | 14 |
| Coating amount (ppm) | 270 | 190 | 190 |

EXAMPLES 14, 15 and 16

The coating treatment was carried out in the same manner as described in Example 1 except that a 0.05 w/v% solution of poly(ethyl methacrylate-dimethylaminoethyl methacrylate) having a weight ratio of 98.6/1.4 (Example 14), 93.2/6.8 (Example 15) or 42.1/57.9 (Example 16) in a Freon R-113-ethanol (96/4 weight ratio) solution was used as the polymer solution. The dialysis performance and complement consumption ratio of the obtained hollow fiber membrane were measured. The obtained results are shown in Table 6.

TABLE 6

|  | Example 14 | Example 15 | Example 16 |
|---|---|---|---|
| Water permeability ($ml/m^2 \cdot mmHg \cdot hr$) | 3.6 | 3.8 | 3.9 |
| Urea clearance (ml/min) | 157 | 159 | 160 |
| $VB_{12}$ clearance (ml/min) | 37 | 39 | 40 |
| Complement consumption ratio | 20 | 16 | 15 |
| Coating amount (ppm) | 170 | 180 | 200 |

EXAMPLES 17, 18 and 19

The coating treatment was carried out in the same manner as described in Example 1 except that a solution formed by dissolving poly(methyl methacrylate-dimethylaminoethyl methacrylate/methoxypolyethylene glycol (polymerization degree=23) methacrylate) (weight ratio=85/10/5) at a concentration of 0.01 w/v% (Example 17), 0.05 w/v% (Example 18) or 0.1 w/v% (Example 19) in a Freon R-113-ethanol (96/4 weight ratio) solution was used as the polymer solution. The dialysis performance and complement consumption ratio of the obtained hollow fiber membrane were measured. The obtained results are shown in Table 7.

TABLE 7

|  | Example 17 | Example 18 | Example 19 |
|---|---|---|---|
| Water permeability ($ml/m^2 \cdot mmHg \cdot hr$) | 4.0 | 3.8 | 3.8 |
| Urea clearance (ml/min) | 162 | 160 | 160 |
| $VB_{12}$ clearance | 41 | 39 | 38 |
| Complement consumption ratio | 14 | 12 | 9 |
| Coating amount (ppm) | 170 | 230 | 250 |

EXAMPLES 20, 21 and 22

The coating treatment was carried out in the same manner as described in Example 1 except that a 0.05 w/v% solution of poly(methyl methacrylate-dimethylaminoethyl methacrylate-methoxypolyethylene glycol (polymerization degree=23) methacrylate) having a weight ratio of 89/10/1 (Example 20), 80/10/10 (Example 21) or 50/45/5 (Example 22) in a Freon R-113-ethanol (80/20 weight ratio) solution was used as the polymer solution. The dialysis performance and complement consumption ratio of the obtained hollow fiber membrane were measured. The obtained results are shown in Table 8.

TABLE 8

|  | Example 20 | Example 21 | Example 22 |
|---|---|---|---|
| Water permeability ($ml/m^2 \cdot mmHg \cdot hr$) | 3.8 | 4.0 | 3.9 |
| Urea clearance (ml/min) | 160 | 161 | 160 |
| $VB_{12}$ clearance (ml/min) | 39 | 41 | 38 |
| Complement consumption ratio | 14 | 12 | 14 |
| Coating amount (ppm) | 190 | 220 | 250 |

EXAMPLES 23, 24 and 25

The coating treatment was carried out in the same manner as described in Example 1 except that a 0.05 w/v% solution of poly(methyl methacrylate-dimethylaminoethyl methacrylate-methoxypolyethylene glycol (polymerization degree=9) methacrylate) (weight ratio=85/10/5) (Example 23), poly(methyl methacrylate-dimethylaminoethyl methacrylate-methoxypolyethylene glycol (polymerization degree=90) methacrylate) (weight ratio=85/10/5) (Example 24) or poly(methyl methacrylate-dimethylaminoethyl methacrylate-polypropylene glycol (polymerization degree=12) methacrylate) (weight ratio=85/10/5) (Example 25) in a Freon R-113-ethanol (80/20 weight ratio) solution was used as the polymer solution. The dialysis performance and complement consumption ratio of the obtained hollow fiber membrane were measured. The obtained results are shown in Table 9.

TABLE 9

|  | Example 23 | Example 24 | Example 25 |
|---|---|---|---|
| Water permeability ($ml/m^2 \cdot mmHg \cdot hr$) | 3.8 | 4.0 | 3.8 |
| Urea clearance (ml/min) | 160 | 162 | 158 |
| $VB_{12}$ clearance (ml/min) | 37 | 40 | 37 |
| Complement consumption ratio | 16 | 16 | 18 |
| Coating amount (ppm) | 210 | 230 | 210 |

EXAMPLES 26, 27 and 28

The coating treatment was carried out in the same manner as described in Example 1 except that a 0.05 w/v% solution of poly(ethyl methacrylate-dimethylaminoethyl methacrylate-methoxypropylene glycol (polymerization degree=23) methacrylate) (weight ratio=85/10/5) (Example 26), poly(butyl methacrylate-dimethylaminoethyl methacrylate-methoxypolyethylene glycol (polymerization degree=23) methacrylate) (weight ratio=85/10/5) (Example 27) or poly(ethyl methacrylate-diethylaminoethyl methacrylate-methoxypolyethylene glycol (polymerization degree=23) methacrylate) (weight ratio=85/10/5) (Example 28) in a Freon R-113-ethanol (96/4 weight ratio) solution was used as the polymer solution. The dialysis performance and complement consumption ratio of the obtained hollow fiber membrane were measured. The obtained results are shown in Table 10.

TABLE 10

|  | Example 26 | Example 27 | Example 28 |
|---|---|---|---|
| Water permeability ($ml/m^2 \cdot mmHg \cdot hr$) | 4.0 | 3.7 | 3.9 |
| Urea clearance (ml/min) | 160 | 158 | 160 |
| $VB_{12}$ clearance (ml/min) | 38 | 37 | 39 |
| Complement consumption ratio | 11 | 12 | 11 |
| Coating amount (ppm) | 220 | 200 | 230 |

EXAMPLE 29

The hollow fiber membranes obtained in Examples 1, 5, 8, 11, 17, and 26 and the untreated hollow fiber membrane were set into dialyzers, and the extracorporeal circulation test was carried out by using a beagle dog having a body weight of about 10 kg. Blood was taken from a shunt formed at the neck portion and introduced to the blood side of the dialyzer. Before the extracorporeal circulation, the interior of the dialyzer was washed with a physiological saline solution, and then the dialyzer and the extracorporeal circuit were filled with a physiological saline solution containing 6000 U/l of heparin. Then, circulation of blood was started. In each dialyzer, leucocyte counts was reduced to a minimum value within about 5 to about 30 minutes from the onset of the dialysis. This minimum value was determined by calculating the realtive value based on the supposition that the number of leucocytes just before the onset of the dialysis was 100. The obtained results are shown in Table 11.

TABLE 11

| Hollow fiber membrane used | Minimum value of leucocyte counts |
|---|---|
| Untreated hollow fiber membrane | 13 |
| Hollow fiber membrane of Example 1 | 83 |
| Hollow fiber membrane of Example 5 | 75 |
| Hollow fiber membrane of Example 8 | 78 |
| Hollow fiber membrane of Example 11 | 77 |
| Hollow fiber membrane of Example 17 | 80 |
| Hollow fiber membrane of Example 26 | 82 |

EXAMPLE 30

A Freon R-113-ethanol (96/4 weight ratio) solution containing 0.1 w/v% of poly(ethyl methacrylate-dimethylaminoethyl methacrylate-methoxypolyethylene glycol (polymerization degree=23) methacrylate) (weight ratio=85/10/5) was supplied at a flow rate of 100 ml/min for 10 minutes to the blood side of a dialyzer from cuprammonium regenerated hollow fibers, and then dry air was fed to the blood side of the dialyzer to remove the excessive polymer solution. These operations of circulation of the polymer solution and feeding of dry air were repeated three times. Air heated at 130° C. was then fed to the blood side of the dialyzer to effect fixation of the polymer.

By using the thus-treated dialyzer, the extracorporeal circulation test was carried out by using a dog in the same manner as described in Example 29. The minimum value of the number of leucocytes was 88, supposing that the value just before the dialysis was 100.

As is apparent from the foregoing description, if the polymeric substance specified in the present invention is coated on the surface of a regenerated cellulose membrane, the phenomenon of activation of the complement system or the phenomenon of leucopenia is moderated and the compatibility with blood is improved. Furthermore, the excellent dialysis performance of the regenerated cellulose membrane is little degraded by this coating treatment.

We claim:

1. A blood-purifying regenerated cellulose membrane which comprises a membrane composed of regenerated cellulose, a blood-contacting surface of said membrane being coated with a polymeric substance comprising as one component units derived from one or more basic vinyl monomers having a side chain containing an amino group.

2. A blood-purifying regenerated cellulose membrane as set forth in claim 1, wherein the polymeric substance is a homopolymer of the basic vinyl monomer having an amino group in the side chain.

3. A blood-purifying regenerated cellulose membrane as set forth in claim 1, wherein the polymeric substance is a copolymer consisting of units derived from at least two basic vinyl monomers having an amino group in the side chain.

4. A blood-purifying regenerated cellulose membrane as set forth in claim 1, wherein the polymeric substance is a copolymer of the basic vinyl monomer or monomers having an amino group in the side chain with another vinyl monomer.

5. A blood-purifying regenerated cellulose membrane as set forth in claim 4, wherein the vinyl monomer to be copolymerized with the basic vinyl monomer or monomers having an amino group in the side chain is at least one monomer selected from the group consisting of 2-hydroxyethyl methacrylate, N-vinylpyrrolidone, alkyl acrylates having 1 to 12 carbon atoms in the alkyl group, alkyl methacrylates having 1 to 12 carbon atoms in the alkyl group, N-alkylacrylic acid amides having 1 to 12 carbon atoms in the alkyl group and N-alkylmethacrylic acid amides having 1 to 12 carbon atoms in the alkyl group.

6. A blood-purifying regenerated cellulose membrane as set forth in claim 1, wherein the polymeric substance is a copolymer comprising a basic vinyl monomer or monomers having a side chain containing an amino group and a vinyl monomer or monomers having a side chain containing polyalkylene glycol.

7. A blood-purifying regenerated cellulose membrane as set forth in claim 6, wherein the polymeric substance contains 0.5 to 50% by weight of units derived from a vinyl monomer having a polyalkylene glycol chain as a side chain.

8. A blood-purifying regenerated cellulose membrane as set forth in claim 6, wherein the vinyl monomer having a polyalkylene glycol chain in the side chain is an acrylic acid ester or methacrylic acid ester.

9. A blood-purifying regenerated cellulose membrane as set forth in claim 6, wherein the polyalkylene glycol chain in the vinyl monomer is a polyethylene glycol or polypropylene glycol having a polymerization degree of 2 to 200 and a terminal group of the polyalkylene glycol chain is selected from the group consisting of hydroxyl, methoxy and ethoxy groups.

10. A blood-purifying regenerated cellulose membrane as set forth in claim 1, wherein the polymeric substance contains at least 0.1% by weight of units derived from one or more basic monomers having an amino group in the side chain.

11. A blood-purifying regenerated cellulose membrane as set forth in claim 1, wherein the basic vinyl monomer or monomers having an amino group in the side chain are selected from the group consisting of acrylic acid derivatives, methacrylic acid derivatives, acrylic acid amide derivatives, methacrylic acid amide derivatives and styrene derivatives, which derivatives have a tertiary amine group in the side chain.

12. A blood-purifying regenerated cellulose membrane as set forth in claim 1, wherein the polymeric substance is coated in an amount of 50 to 5000 ppm based on the regenerated cellulose membrane.

13. A blood-purifying regenerated cellulose membrane as set forth in claim 1 wherein the regenerated cellulose membrane is in the form of a hollow fiber.

* * * * *